United States Patent [19]

Craig et al.

[11] Patent Number: Plant 7,351

[45] Date of Patent: Oct. 9, 1990

[54] GERANIUM PLANT #821-(82-116-13)

[75] Inventors: Richard Craig; Leon Glicenstein, both of State College, Pa.

[73] Assignee: Research Corporation Technologies, Inc., Tucson, Ariz.

[21] Appl. No.: 347,103

[22] Filed: May 3, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Scully, Scott, Murphy & Presser

[57] ABSTRACT

This invention relates to a new and distinct cultivar of Geranium (*Pelargonium*×*hortorum*) named #821-(82-116-13) substantially as described herein, characterized as being particularly well adapted to both commercial greenhouse production and garden performance, and as being early flowering and floriferous, self-branching and compact, heat-tolerant and low-light-tolerant.

1 Drawing Sheet

The present invention relates to a new and distinct cultivar of Geranium (*Pelargonium*×*hortorum*) called #821-(82-116-13). The cultivar is particularly well adapted to both commercial greenhouse production and garden performance. The cultivar is characterized as being early flowering, floriferous, self-branching and compact.

The cultivar was developed from an organized, scientifically designed breeding program carried out at the Department of Horticulture, The Pennsylvania State University, University Park, Pa. 16802. The breeding program was designed to create new geranium genotypes with clear, bright colors which combined the flowering ability and compactness of European cultivars with the heat tolerance, low-light tolerance and excellent greenhouse production qualities of cultivars developed at Penn State. The pedigree of this cultivar is as follows:

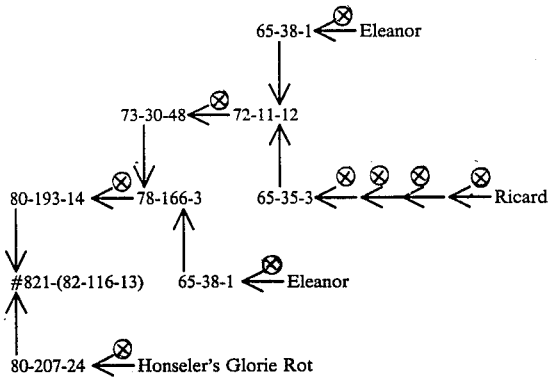

The selection was asexually propagated by cuttings and the reproductions ran true.

With reference to the detailed description of the cultivar which follows, the test plant was grown in a glasshouse under full natural light, at a night temperature of about 58° F., and a day temperature of about 68° F. Soilless medium was fertilized with every watering with 200 ppm nitrogen from 15-16-17.

BRIEF DESCRIPTION OF THE DRAWING

The color photograph illustrates the short, branching habit of the plant and the large, showy red flower clusters carried well above the lightly zoned, densely placed leaves of the variety.

Color readings were taken under incandescent light at 200 foot candles and color identification was by reference to The Royal Horticultural Society Colour Charts, except where common terms of color definition are employed.

THE PLANT

Classification:

*Botanical.*—*Pelargonium*×*hortorum.*

*Tradename.*—"#821-(82-116-13)".

Form: Compact, self-branching.

Height: Average 16.0 cm; range 13.0–21.0 cm.

Growth: Freely branching from base; short internodes; stands upright with no artificial support.

Leaves:

*Size.*—Largest measured 6.0 cm long×10.5 cm wide; ratio of length to width approximately 2:3.

*Shape.*—Reniform, variously lobed.

*Margin.*—Crenate.

*Texture.*—Pubescent; dull.

*Color.*—Adaxial: Distal: Green 137B. Zone: Greyed-purple 187A overlaid with green 137B. Proximal: Green 137C. Abaxial: Green 137C.

*Ribs and veins.*—Palmate venation; veins recessed and prominent.

*Petioles.*—Length: Up to 6.6 cm long. Color: Green 137C.

Stem:

*Internode length.*—Up to 1.5 cm long.

*Color.*—Green 137C.

THE FLOWER

Blooming habit: Continuous.

Inflorescence form: Umbellate.

Inflorescence size: Depends on number of florets; inflorescences often 11.0 cm across.

Persistence: Persistent, non-shattering.

Disease resistance: Not known; favorable in outdoor trials.

Lasting quality: Excellent; usually 3 weeks or longer.

Florets:

*Number.*—Often over 32 per inflorescence.

*Form.*—Flat to cupped.

*Size.*—2.5–3.5 cm across open floret.

Petals:

*Number.*—5–7.

*Texture and appearance.*—Smooth-edge.

*Color.*—Upper petals: Adaxial: Distal two-thirds: Red 44A with regular spot red 45B. Proximal one-third: Red 39A with veins red 45B. Base: Small area of white 155D. Abaxial: Red 41A with base white 155D. Lower petals: Adaxial: Similar to upper petal adaxial surface with much less pronounced spot and veins. Abaxial: Similar to upper petal abaxial surface.

Petaloids:

*Number.*—1–2.

*Shape.*—Variable; often misshaped.

*Color.*—Similar to the color of the petals.

Sepals:

*Number.*—5–7.

*Pedicel.*—Length: 1.9–2.9 cm. Color: Green 137C.

Peduncle: Arises from node; opposed to leaf petiole; pubescent.

*Length.*—Up to 18.2 cm.

*Color.*—Green 137C.

REPRODUCTIVE ORGANS

Androecium:

*Stamens.*—3–8 flat, ribbon-like filaments with rose-purple tips, joined at their bases; versatile attachments to anthers which are light purple and well-developed; 2 sizes of orange pollen.

*Staminodes.*—1–2 flat, ribbon-like filaments with no anthers.

*Petaloid stamens.*—1–3 petal-like filaments with partially developed anthers.

Gynoecium:

*Pistil number.*—1.

*Length.*—6.0–8.5 mm.

*Stigma.*—4–5-parted; light purple.

*Style.*—1.0–2.5 mm long; green or purple.

*Ovary.*—3.0–4.5 mm long; superior; very pubescent.

*Fruit.*—Achene schizocarp; rarely observed.

What is claimed is:

1. A new and distinct cultivar of Geranium substantially as herein shown and described, characterized as being particularly well adapted to both commercial greenhouse production as well as garden performance, and as being early flowering, floriferous, self-branching, compact, heat-tolerant and low-light-tolerant.

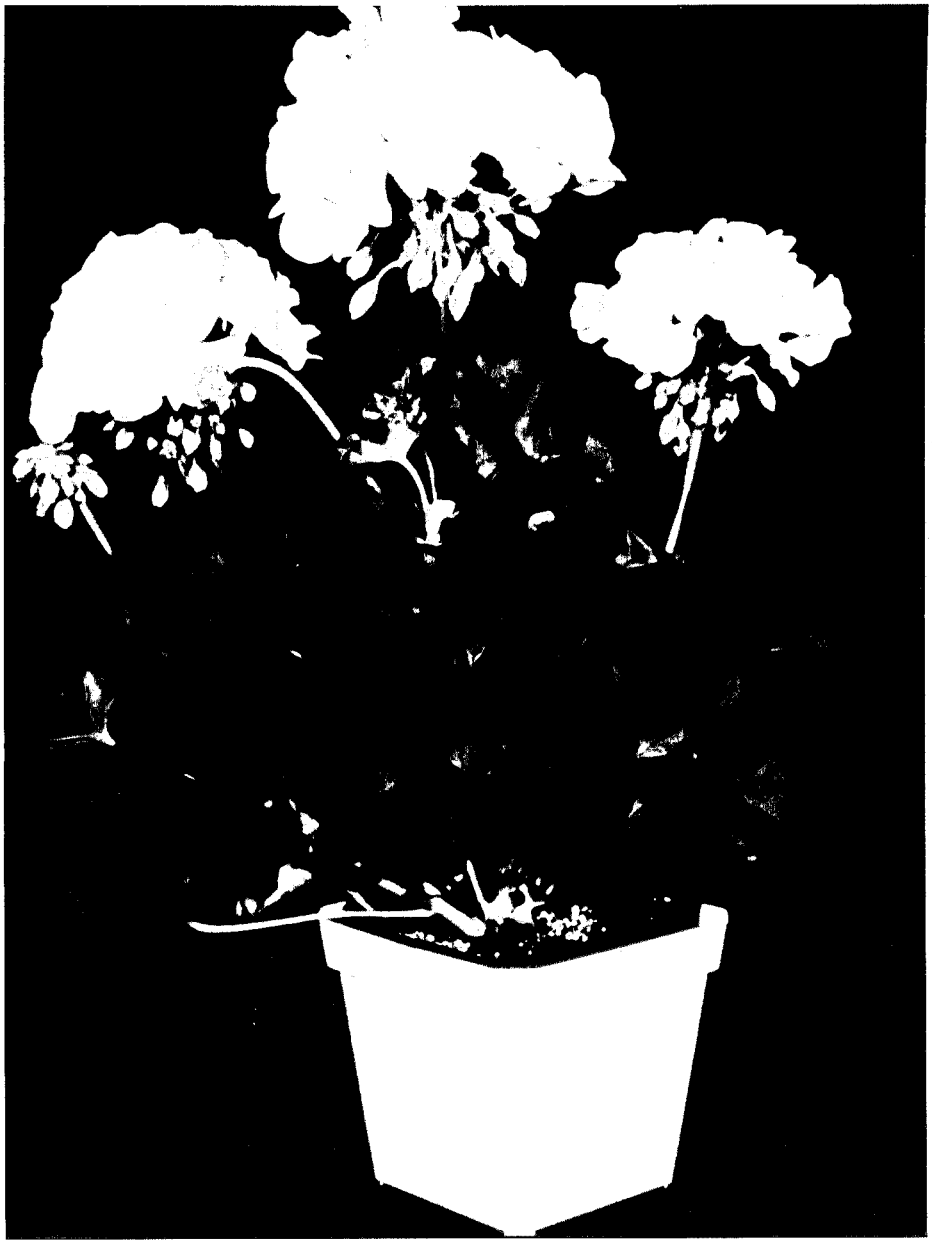

* * * * *